(12) United States Patent
Kroening et al.

(10) Patent No.: US 6,347,550 B1
(45) Date of Patent: Feb. 19, 2002

(54) ULTRASONIC TEST DEVICE

(75) Inventors: Michael Kroening, Saarbruecken; Juergen Salzburger, Neunkirchen; Friedhelm Waite, Gersheim, all of (DE)

(73) Assignee: Fraunhofer-Gesellschaft zur Foerderung der Angewandtzen Forschung E.V., Munich (DE)

( * ) Notice: Subject to any disclaimer, the term of this patent is extended or adjusted under 35 U.S.C. 154(b) by 0 days.

(21) Appl. No.: 09/744,150

(22) PCT Filed: Jul. 21, 1999

(86) PCT No.: PCT/EP99/05198

§ 371 Date: Mar. 23, 2001

§ 102(e) Date: Mar. 23, 2001

(87) PCT Pub. No.: WO00/05577

PCT Pub. Date: Feb. 3, 2000

(30) Foreign Application Priority Data

Jul. 22, 1998 (DE) .......................... 198 33 034

(51) Int. Cl.[7] .............................................. G01N 29/04
(52) U.S. Cl. .............................. 73/598; 73/624; 73/627; 73/636
(58) Field of Search .................. 73/598, 593, 597, 73/624, 649, 660, 661, 635, 636, 622, 627, 760, 799

(56) References Cited

U.S. PATENT DOCUMENTS

| 3,558,876 A | * | 1/1971 | Tillman .................. 246/169 S |
| 4,781,060 A | * | 11/1988 | Berndt ........................ 73/146 |
| 5,349,861 A | * | 9/1994 | Catot et al. .................... 73/598 |
| 5,363,702 A | * | 11/1994 | Catot et al. .................... 73/598 |
| 5,804,731 A | * | 9/1998 | Jaeggi .......................... 73/636 |
| 5,864,065 A | * | 1/1999 | Prorok et al. .................. 73/622 |

* cited by examiner

*Primary Examiner*—Hezron Williams
*Assistant Examiner*—Jacques Saint-Surin
(74) *Attorney, Agent, or Firm*—Crowell & Moring LLP

(57) ABSTRACT

An ultrasonic test process and device intended for testing a preferably cylindrical specimen (2), such as railway wheel, which is capable of displacement along a support, such as a rail (10). The ultrasonic test device comprises at least one ultrasonic probe (14) disposed in the support (10) which emits acoustic waves in the direction of the specimen. The acoustic waves are reflected by defects in the specimen (2) and received again by a probe. The test device is designed to reliably and non-destructively test the volume and surface of the specimen (2) as it rolls over the support (10). In the process of the invention a number (m) of probes (14) are controlled so that the ultrasonic waves have a preferably horizontal polarization and are emitted into the specimen (2) at a predetermined angle (66) relative to the running surface (8) of the rail (10).

9 Claims, 5 Drawing Sheets

ULTRASONIC TEST DEVICE

BACKGROUND OF THE INVENTION

The invention relates to a process for ultrasonic testing particularly of a specimen in the form of a railway wheel in accordance with the features set forth in the preamble of claim 1.

Such a process for ultrasonic testing is known from U.S. Pat. No. 3,978,712 according to which two ultrasonic probe elements are used. The two probe elements are arranged opposite one another and angled to a normal to the rail in the contact zone of a railway wheel. The one probe element is used to emit the ultrasonic waves at a predefined angle to the normal and introduce them into the railway wheel in circumferential direction, with the ultrasonic waves traveling through the railway wheel in circumferential direction. The ultrasonic waves, which propagate linearly in principle, are intended to be deflected into circular wave propagation due to reflection along the wheel perimeter or the wheel-air boundary layer. After at least one rotation, a portion of the ultrasonic waves exits from the wheel in the contact zone and reaches the second probe acting as a receiver. This forced circular wave propagation causes substantial losses so that the first probe element embodied as the transmitter must be correspondingly large and designed for high acoustic power. Furthermore, due to the reflections along the wheel perimeter required for circular wave propagation, a high interference level must be expected so that the evaluation of the ultrasonic waves received by the second probe element and detection of useful signals corresponding to flaws in the wheel requires considerable complexity. Ultrasonic waves striking flaws within the railway wheel and suitable for subsequent evaluation are not reflected at the flaws but are attenuated and transmitted in circumferential direction until they reach the second receiver probe element.

Furthermore, DE-A 195 44 217 discloses a process for ultrasonic testing of a specimen, particularly in the form of a railway rail over which a test wheel rolls. The test wheel, in the area of its substantially cylindrical rolling surface, which rolls over the specimen, contains a plurality of probe elements, a number or subgroup of which form a probe. The transmit or receive sides facing the probe come to lie within the contact zone of the rolling surface and the surface of the specimen. The probe elements of the respectively activated probe are operated in what is referred to as a phased array technique making it possible to predetermine an angled introduction of the ultrasonic waves into the test specimen through time-defined, runtime delayed control. A detection unit comprising particularly a laser and a photo detector detects the angular position of the test wheel. Said detection unit does not detect either the speed or the reaching of any given zone. The test wheel further comprises a number of distance sensors to isolate the probe elements forming the respectively active probe if a predefined minimum distance to the travel surface fails to be reached. The arrangement of said distance sensors and their signal processing for isolation require considerable additional complexity. A cylindrical test specimen cannot readily be inspected and the power supply, which powers the test wheel rolling over the rail, either via sliding contacts or an alternating voltage supply, requires additional measures.

SUMMARY OF THE INVENTION

Based thereon it is the object of the invention further to develop the process for ultrasonic testing of the aforementioned type to ensure functionally reliable detection of flaws within the volume and on the surface of the specimen during the rollover of a specimen, particularly a railway wheel. The complexity required to handle and evaluate the test should be reduced to a minimum. Reliable testing of railway wheels made of different parts and/or different materials should be possible and the detection particularly of internal cracks starting at the wheel disk / wheel rim junction should be highly reliable.

This object is attained in accordance with the invention as described and claimed hereinafter.

The process for ultrasonic testing according to the invention is distinguished by its reliable detection of flaws, particularly internal defects, such as cracks in the test specimen. For instance, if the specimen is embodied as a railway wheel consisting of different parts and/or different materials, defects starting, for example, from the junction zone between wheel disk and wheel rim can be detected. In a recess or groove of the railhead, a linear array of an arrangement of ultrasonic probes is provided, which inject ultrasonic waves into the specimen preferably without coupling means. The angle of incidence of the ultrasonic waves can advantageously be predefined. The length of the array is at least equal to the circumference of the test specimen, and the probe elements preferably take the form of electromagnetic ultrasonic transducers. Testing takes place during the rollover of the specimen. A detection unit comprising particularly two position detectors, such as photoelectric barriers, detects the rolling in of the specimen into the probe array path and determines the speed of the specimen or wheel. Advantageously, the determined and/or calculated speed is used to control activation or deactivation synchronous with the wheel motion of a predefined number of elements of the array, which form a subgroup. The number M of the corresponding elements of a subgroup is predetermined as a function of the largest permissible distance between the two peripheral elements and the wheel surface and/or the required directional characteristics and/or the required test sensitivity. Preferably, the number M is predefined between 3 and 11, particularly between 5 and 9.

As the specimen or wheel rolls into the probe array path, the first subgroup of the linear array with M individual elements is activated in such a way that the contact point between wheel and rail is symmetrically in the center of the subgroup. The activation/trigger instant (master trigger) is calculated from the previously determined speed of the wheel and the distance from the center of the subgroup to the position of the photoelectric barriers. This function is performed by a trigger module. Through an electronic runtime delay in the excitation of the individual subgroup elements, the ultrasound is coupled into the wheel as a transverse wave with horizontal polarization at predefinable angles of between 35° and 90° to the surface normal. The corresponding trigger instants of the array elements are calculated from the master trigger. This electronic swing of the sound beam produced by the subgroup makes it possible to detect defects within the volume as well as on the running surface and along the inside of the wheel. As the wheel moves over the rail, a respective element of the subgroup is switched off and a new element is added as calculated from the master trigger, the determined wheel speed and the known distance of the array elements. Due to this procedure and a multiplexer, which is controlled via the trigger module, a channel number M is sufficient for the ultrasonic test device. This considerably simplifies the circuit complexity. Due to the rolling of the specimen over the rail containing the probe elements, the relative speed at the contact point, i.e. for the center element of the subgroup, is exactly zero and for the subgroup elements to the right and left thereof is very low. Consequently, there is no acoustic Barkhausen noise interference due to magnetic reversal as a result of spatially in homogeneous magnetic fields of the probe element.

In a preferred embodiment, the individual elements of the linear probe array are accommodated in a recess or groove in the rail to protect them from mechanical wear. The position of the specimen, and thus the position of the probe elements in relation to the specimen, can be determined by said trigger module whose output signals are stored in a control and evaluation circuit together with the measuring signals received by the probe elements, so that defects within the specimen can be pinpointed based on a reference position after completion of the test.

Further developments and special embodiments of the invention are set forth in the dependent claims.

BRIEF DESCRIPTION OF THE DRAWINGS

The invention will now be described in greater detail with reference to, but without limitation to, the exemplary embodiments depicted in the drawing in which.

DETAILED DESCRIPTION OF PREFERRED EMBODIMENTS

Figure 1:
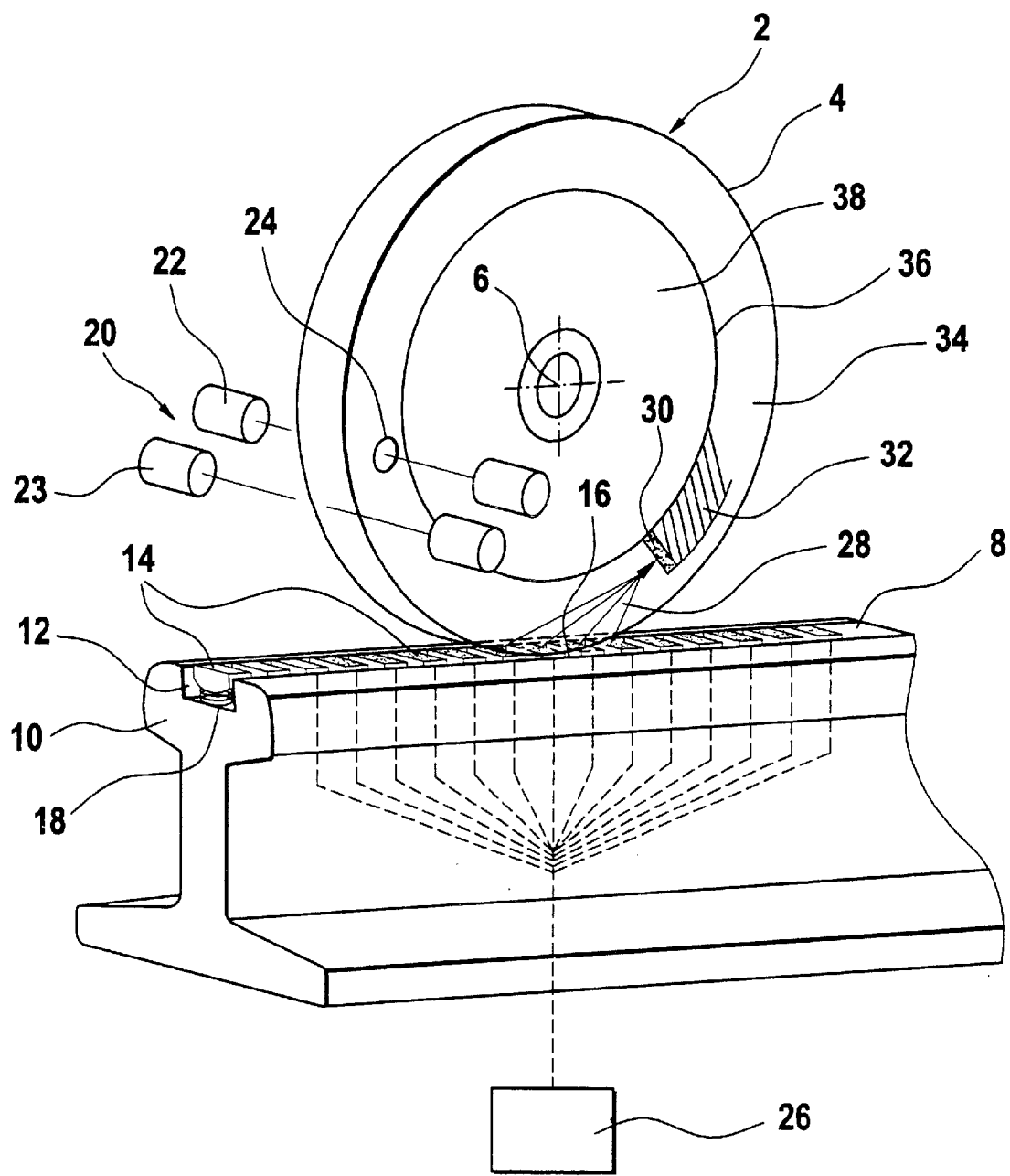
FIG. 1 is a perspective view of a test specimen rolling over a rail.

FIG. 1 shows an at least approximately cylindrical test specimen 2, particularly in the form of a railway wheel having a running surface 4 and being rotatable about an axis 6 that is orthogonal to the drawing plane. The specimen 2 with its running surface 4 can roll over a travel surface 8 of a rail 10, which in this case is embodied as a railway rail. Rail 10 has a recess or groove 12 extending in longitudinal direction within its travel surface 8 with a predefined number m of probe elements 14. The preferably electromagnetic probe elements 14 are integrated within groove 12 in the form of a linear array. The number m is at least equal to the quotient of the circumference of the running surface 4 of the specimen 2 and the width of the individual probe elements 14 measured in longitudinal direction of rail 10. In the typical embodiment of the specimen 2 as a railway wheel with a diameter of 880 mm and a smallest width of the probe elements 14 of 5 mm, the number m=552. According to the invention, as the running surface 4 of the specimen 2 rolls over or along the travel surface 8, only a respective subgroup of the probe elements 14 located in the area of the contact point or the contact line 16 of the running surface 4 on the travel surface 8 is activated. The number M of the subgroup elements is predetermined taking into account the largest permissible distance between the probe elements located at the two edges of the subgroup and the running surface or wheel surface 4, the required directional characteristics of the sound waves emitted by the probe elements, and the required test sensitivity. The individual probe elements 14 are advantageously elastically supported within groove 12 by means of spring elements 18.

The test device further comprises a detection unit 20 to determine the position of the specimen 2 in relation to a definable initial position, particularly the array of probe elements 14. The detection unit 20 comprises particularly two photoelectric barriers 22, 23 and a mirror 24 arranged on the specimen 2. The detection unit 20, like the probe elements 14, is connected with a control and evaluation circuit 26 in which the supplied signals are evaluated and used to control the test device. Determined is, for example, the respective position of specimen 2 in relation to the initial position and the lateral speed of the specimen or railway wheel 2 in longitudinal direction of the rails. According to the invention, as the test specimen 2 rolls over the rail 10, taking into account the position data and the lateral wheel speed, a corresponding subgroup with the number M of the total probe elements m is activated in such a way that the respectively activated probe elements lie particularly symmetrical to the corresponding contact point or contact line 16 between specimen 2 and rail 10.

A subgroup of the probe elements 14 in the contact area or in the zone of the contact point 16 is excited via a runtime delay such that an ultrasonic wave 28 with horizontal polarization and sufficient directional effect is coupled into specimen 2, so that defects 30 within volume area 32 are exposed to the ultrasonic waves, i.e. starting from the running surface 4, and reflect them in the direction of said subgroups. If, for example, the test specimen 2 is embodied as a railway wheel with a tire or wheel rim 34, even defects in the area of the interior bore surface 36 and/or the wheel disk 38 can be detected and measured. The probe elements of the subgroup receive the reflected ultrasound and supply the measuring signals to the control and evaluation circuit 26. The position detection unit 20 determines the rolling in of the test specimen into the probe array path as well as the speed of the wheel in connection with the evaluation circuit 26 to control the activation or deactivation, which is synchronous with the wheel motion, of the predefined number of probe elements of each subgroup of the array. As the test specimen 2 rolls over rail 10, the position data and the lateral wheel speed are used to activate a corresponding subgroup with the number M of probe elements 4 such that said probe elements are symmetrical to the respective support or contact point 16. As the specimen 2 rolls over rail 10, a corresponding probe element of the subgroup is switched off and a new probe element is added until the circumference or running surface 4 has rolled over the entire linear array of probe elements 14. After reflection of the ultrasonic waves from flaws 30 within the volume area 32 or at the junction of wheel rim 34 and wheel disk 38, the control and evaluation circuit 26 evaluates the ultrasonic waves as a function of the position of the specimen 2 as determined by the detection unit 20. It should be noted that the inspection by means of the ultrasonic test device according to the invention is conducted without the use of any coupling means, such as water or the like, between the specimen and the rail.

Figure 2:
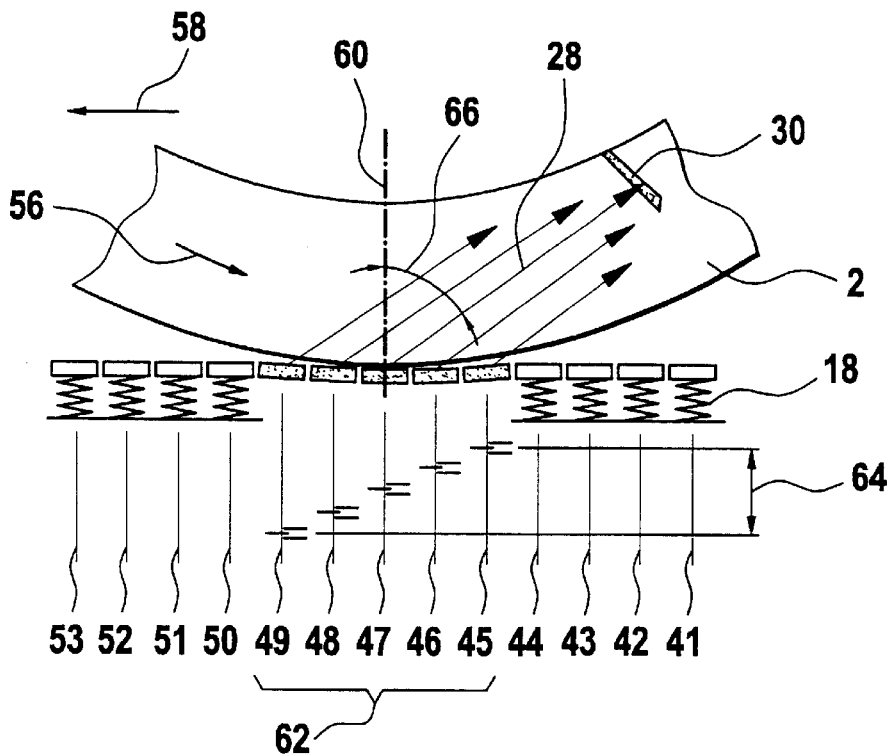
FIGS. 2, 3 are schematic longitudinal sections in the area of the contact point between specimen and rail.

FIG. 2 shows a magnified part of specimen 2 and some of the probe elements numbered 41 to 53 adjacent to contact point 16. It is assumed that specimen 2 is rotating about its axis of rotation in the direction of arrow 56 so that specimen 2 is laterally rolling over rail 10 in the direction of arrow 58, and the axis of rotation is on the normal 60 at the contact point 16. The individual probe elements are elastically supported within the rail (not depicted) by means of said spring elements 18. For reasons of clarity the spring elements of the five probe elements 45 to 49 lying next to the normal 60 are not shown. Said five probe elements 45 to 49 form a subgroup 62. According to the invention, said probe elements of the subgroup 62 are not excited simultaneously but consecutively with a runtime delay 64 such that the sound is directed obliquely into the specimen 2, i.e. at an angle 66 to the normal 60. The total runtime delay 64 is predefined as a function of the corresponding requirements for the desired angle of incidence 66. The number M of the probe elements of the subgroup 62 is also predefined as a function of the respective requirements taking into account, when defining the number M of the subgroup 62, the greatest permissible distance between the two peripheral elements of the subgroup (according to FIG. 2 the outer elements 45 and 49) to the running surface 4 of the specimen 2, further the required directional characteristics or the angle of incidence 66, and the required test sensitivity. The number M is preferably predefined between 3 and 11 and particularly between 5 and 9. The aforementioned evaluation and control circuit electronically predefines the runtime delay 64 in the time-shifted excitation of the individual elements of subgroup 62. According to the invention the ultrasound is coupled into specimen 2 as a transverse wave with preferably horizontal polarization at an angle of incidence 66 to the normal 60 ranging between 90° and 350°.

Figure 3:
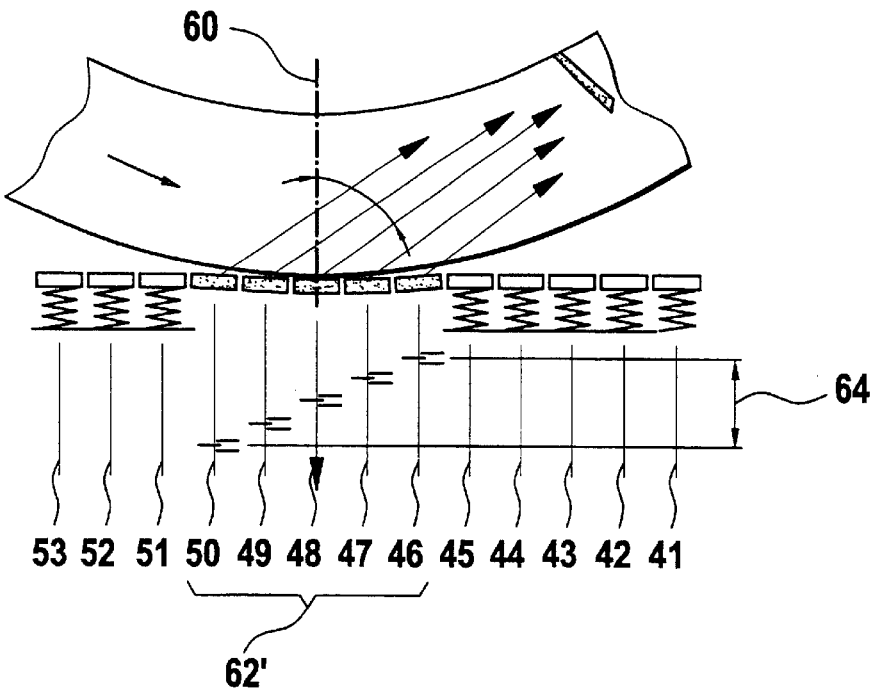

FIG. 3 shows the specimen 2 in a position assumed by specimen 2 shortly after the position shown in FIG. 2. Now the subgroup 62' with the probe elements 46 to 50 is activated or controlled with runtime delay 64. In contrast to FIG. 2, probe element 45 is switched off, while probe element 50 has been added. The central probe element of subgroup 62' is now probe element 48 through which the normal 60 extends. As may be seen, here too, the contact point 16 is at the center of subgroup 62'. The activation or trigger instant, referred to as the master trigger, is determined and particularly calculated by the evaluation and control circuit 26 from the previously determined speed of specimen 2 and the distance of the center of subgroup 62' to the position of the aforementioned detection unit. The time-delayed control instants of the individual probe elements of the respectively activated subgroups are calculated from the master trigger.

Figure 4:
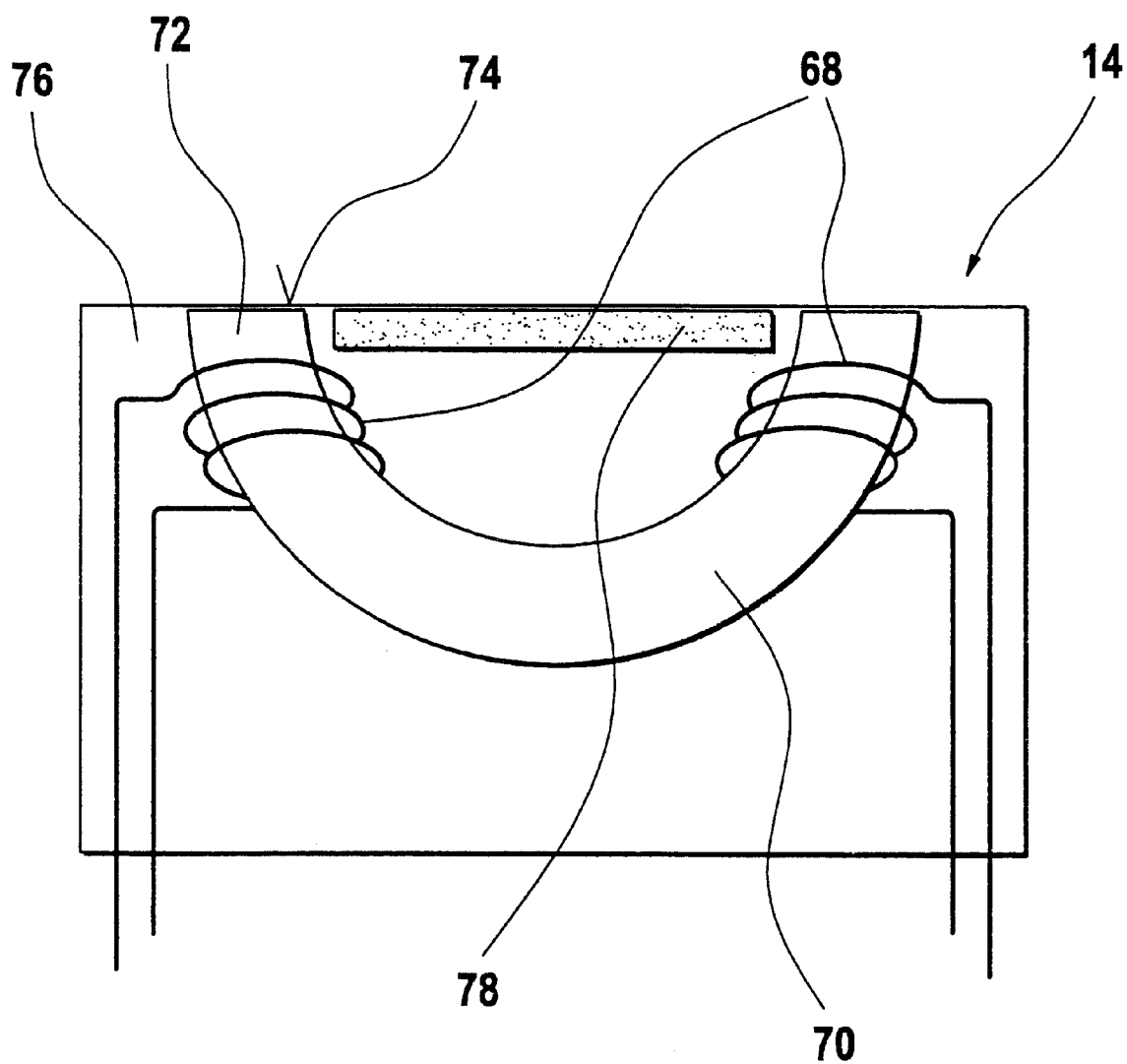
FIG. 4 is an exemplary embodiment of a probe element.

FIG. 4 is a section through the electromagnetic probe element 14 for producing horizontally polarized transverse waves. The probe element 14 comprises a magnetizable semicircular toroidal tape core 70 wound with a high frequency coil 68 and arranged in a potting block 76 so that its ends 72 point toward the measuring side 74. Disposed between the ends 72 of the toroidal tape core 70 are rod-shaped permanent magnets 78 extending in their longitudinal direction between the ends 72 of the toroidal tape core 70.

Figure 5:
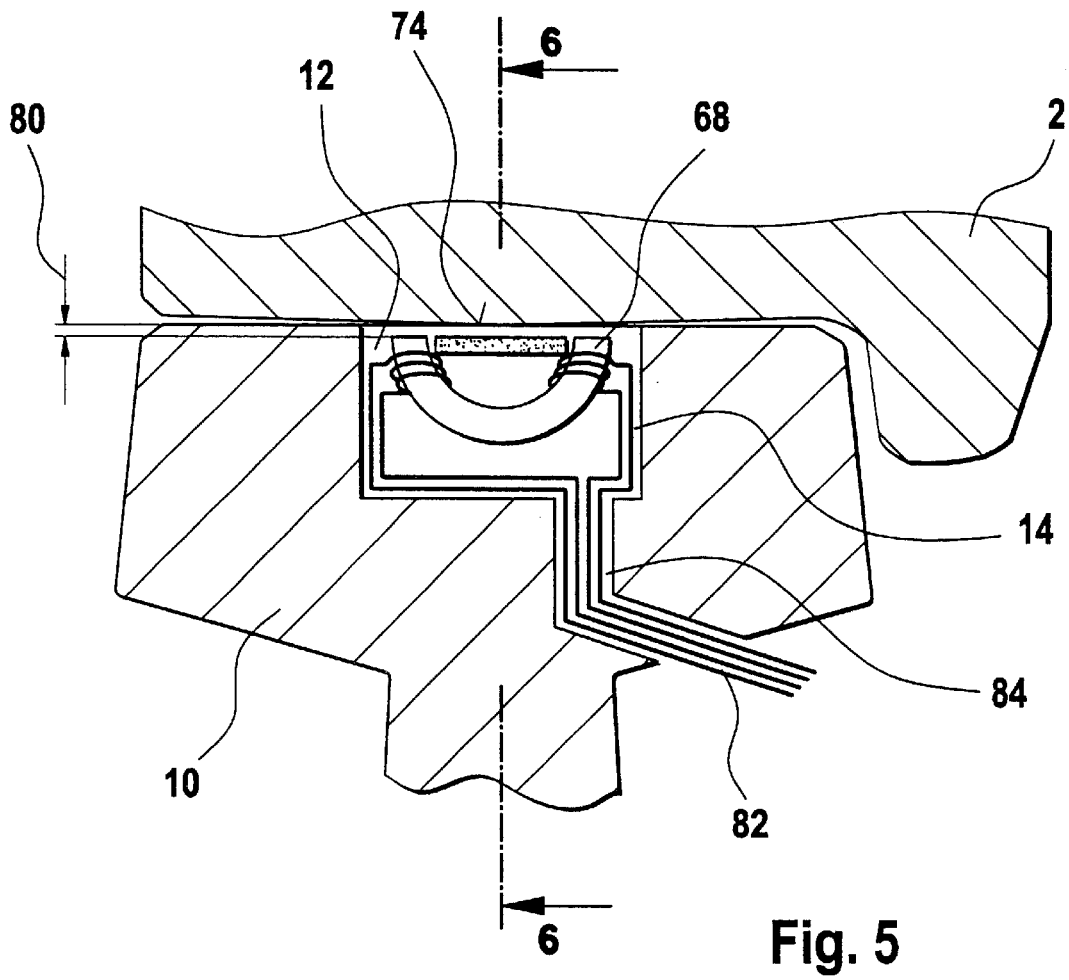
FIG. 5 is a magnified section normal to the longitudinal direction of the rail.

FIG. 5 is a cross section through a probe element 14 integrated within rail 10. Probe element 14 is permanently mounted within groove 12 of rail 10 such that the measuring side 74 is spaced at a distance 80 from the rail or traveling surface 8. Said distance 80 measures, in particular, from 0.1 to 0.2 mm. The electrical connections 82 of the HF coil 68 for inducing the signal in the case of transmission and receiving the signal in the case of reception are arranged in a cable duct 84 integrated within rail 10 and are connected with the aforementioned evaluation and control circuit in a manner not further depicted.

Figure 6:
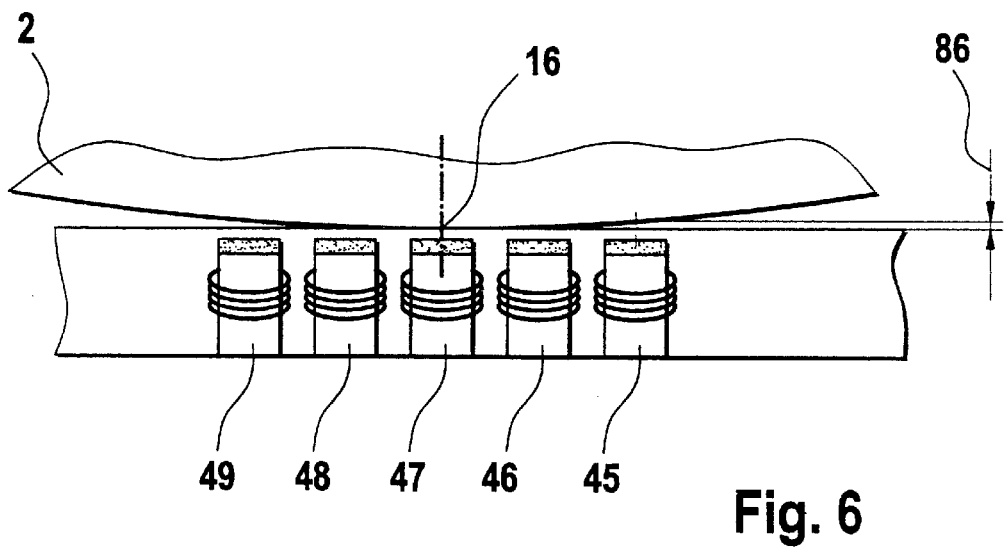
FIG. 6 is a section along line A according to FIG. 5.

FIG. 6 is a section along line A according to FIG. 5 with the five activated probe elements 45 to 49 of the subgroup. The peripheral probe elements 45 and 49 remote from the central element 47 above which is located the contact point 16 have a greater gap 86 with respect to the wheel 2 corresponding to the wheel diameter. This greater gap causes a reduced excitation of the peripheral elements 45 and 49 of the subgroup and, correspondingly, also of the elements 46 and 48, which are located further inward. According to the invention, by way of compensation, the peripheral elements 45,46 and 48, 49 of the subgroups depicted here, or any activated subgroups, are subject to a higher amplitude in their delayed excitation.

Figure 7:
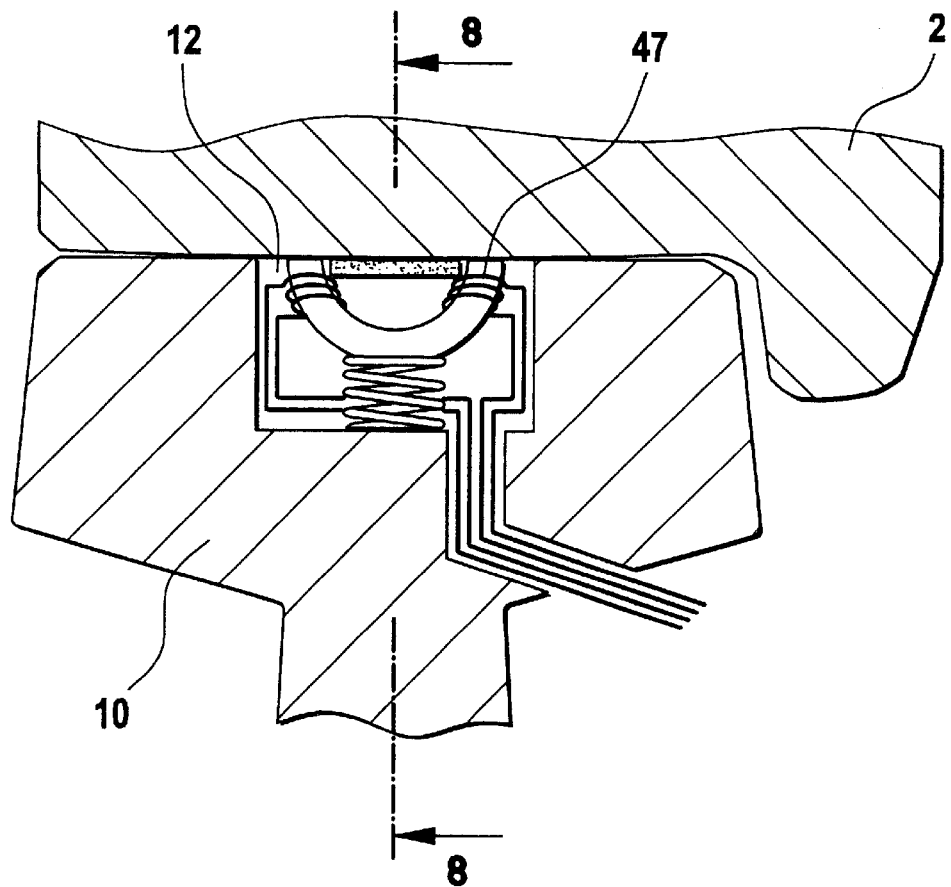
FIG. 7 is a magnified section through a further embodiment normal to the longitudinal direction of the rail.
Figure 8:
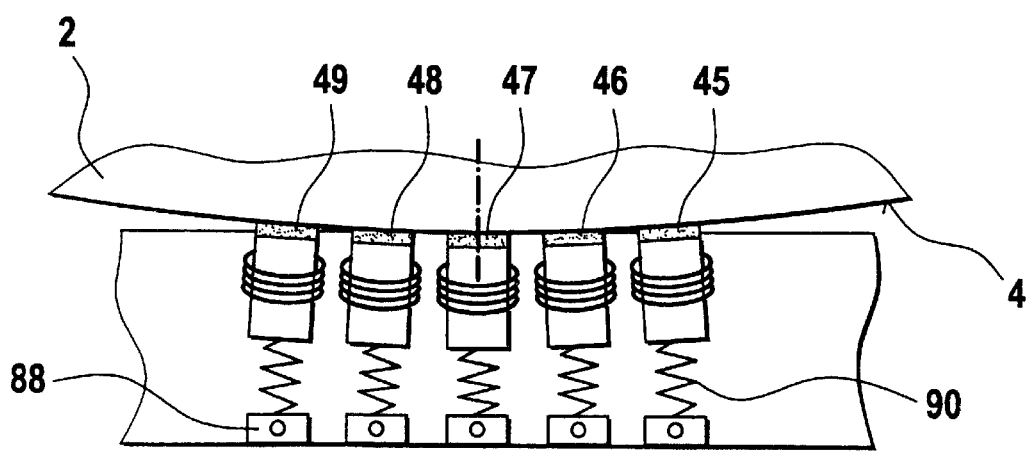
FIG. 8 is a section along line B according to FIG. 7.

FIGS. 7 and 8 show a different embodiment, similar to FIGS. 5 and 6, of the probe elements 45 to 49 integrated within the groove 12 of rail 10. These probe elements are arranged within groove 12 of rail 10 by means of a gimbal mount 88 and a spring element 90. As the running surface 4 of the specimen 2 rolls over the travel surface 8 of the rail 10, the corresponding probe elements of the active subgroup adhere to the running surface 4 due to the magnetic retention forces, particularly due to the toroidal tape core and/or permanent magnets discussed in connection with FIG. 4, to permit uniform excitation of all probe elements of the respectively activated subgroup.

What is claimed is:

1. A process for ultrasonic testing of a test specimen comprised of different parts or different materials, said test specimen having a running surface which moves along a travel surface of a support with a moving line of contact between the running surface of the specimen and the travel surface of the support;

wherein at least two ultrasonic probe elements are arranged within the support to emit ultrasonic waves into the specimen at a predefined angle to the normal of the support and to receive ultrasonic waves reflected from striking flaws within the specimen;

wherein out of a number (m) of probe elements which are arranged as a linear array within a groove in the support, a predefined number (M) of a subgroup of probe elements is activated or deactivated, respectively, the number (m) being at least equal to the quotient of the circumference of the running surface and the width of the individual probe elements arranged side by side as measured in longitudinal direction of the support;

wherein for ultrasonic testing of the specimen, the probe elements of the respectively activated subgroup are controlled with a runtime delay such that the ultrasonic waves are introduced with horizontal polarization into a volume area of the specimen and are reflected by any flaws;

wherein a detection unit is used to determine the entrance of the specimen into the probe array and to calculate the speed of the specimen; and wherein the respective subgroups of probes which are located proximate the contact line of the running surface on the traveling surface are synchronously activated and deactivated as a function of the speed of the specimen.

2. A process according to claim 1, wherein said test specimen is a railway wheel having a running surface which rolls along a travel surface of a rail, and the ultrasonic probe elements are arranged within the rail.

3. A process according to claim 1, wherein within the respectively activated subgroup, the probe elements with the number (m) between 3 and 11 are activated.

4. A process according to claim 3, wherein within the respectively activated subgroup, the probe elements with the number (m) between 5 and 9 are activated.

5. A process according to claim 1, wherein the probe elements are flexibly supported within the support, and the probe elements of the respectively activated subgroup are brought into direct contact with the running surface of the specimen.

6. A process according to claim 5, wherein the probe elements are flexibly support by spring elements.

7. A process according to claim 1, wherein the probe elements are mounted via gimbal mounts within the rail, and the probe elements of the respectively activated subgroup are brought into direct contact with the running surface of the specimen.

8. A process according to claim 1, wherein the probe elements in the respectively activated subgroup lying adjacent a central probe element through which the normal to the contact line extends, are subject to a higher amplitude than said central probe element.

9. A process according to claim 8, wherein said adjacent probe elements are arranged symmetrically relative to said central probe element.

* * * * *